(12) United States Patent
Ishikawa et al.

(10) Patent No.: US 10,161,900 B2
(45) Date of Patent: Dec. 25, 2018

(54) GAS SENSOR ELEMENT AND GAS SENSOR

(71) Applicant: NGK SPARK PLUG CO., LTD., Nagoya-shi, Aichi (JP)

(72) Inventors: Takanori Ishikawa, Inuyama (JP); Naoki Yamada, Iwakura (JP); Koji Shiono, Komaki (JP)

(73) Assignee: NGK SPARK PLUG CO., LTD., Aichi (JP)

( * ) Notice: Subject to any disclaimer, the term of this patent is extended or adjusted under 35 U.S.C. 154(b) by 334 days.

(21) Appl. No.: 14/476,845

(22) Filed: Sep. 4, 2014

(65) Prior Publication Data

US 2015/0060274 A1 Mar. 5, 2015

(30) Foreign Application Priority Data

Sep. 5, 2013 (JP) .................................. 2013-183868
Aug. 1, 2014 (JP) .................................. 2014-157864

(51) Int. Cl.
*G01N 27/407* (2006.01)
*G01N 27/409* (2006.01)

(52) U.S. Cl.
CPC ....... *G01N 27/4077* (2013.01); *G01N 27/409* (2013.01)

(58) Field of Classification Search
CPC ................................................. G01N 27/4077
See application file for complete search history.

(56) References Cited

U.S. PATENT DOCUMENTS

| 4,164,462 A * | 8/1979 | Ichikawa | H01M 4/9058 204/429 |
| 4,402,820 A * | 9/1983 | Sano | G01N 27/4077 204/425 |
| 4,629,535 A * | 12/1986 | Oyama | F02D 41/1476 204/425 |
| 5,766,434 A | 6/1998 | Fujii et al. | |

(Continued)

FOREIGN PATENT DOCUMENTS

| JP | 56-90255 A | 7/1981 |
| JP | 56-111461 A | 9/1981 |

(Continued)

OTHER PUBLICATIONS

Office Action dated Apr. 26, 2017 issued by Japanese Intellectual Property Office in counterpart Japanese Application No. 2014-157864.

(Continued)

*Primary Examiner* — Louis J Rufo
(74) *Attorney, Agent, or Firm* — Sughrue Mion, PLLC (57) ABSTRACT

A gas sensor element (3) includes: a solid electrolyte body (3s) having a bottomed tubular shape and a closed front end, and extending in the direction of an axial line O; an inside electrode (50) which is provided on an inner surface of the solid electrolyte body; an outside electrode (51) which is provided on an outer surface of the solid electrolyte body; and a porous protective layer (80) which covers the outside electrode, the porous protective layer has an inside region (81) which covers the outside electrode and an outside region (82) which covers the inside region and has a lower porosity than the inside region, and the outside region is formed of a sintered body of ceramic and glass.

10 Claims, 3 Drawing Sheets

(56) References Cited

U.S. PATENT DOCUMENTS

| | | | | |
|---|---|---|---|---|
| 5,948,225 | A * | 9/1999 | Katafuchi | G01N 27/4075 |
| | | | | 204/421 |
| 6,086,948 | A * | 7/2000 | Roth | C04B 41/009 |
| | | | | 427/126.2 |
| 6,660,145 | B2 * | 12/2003 | Hotta | G01N 27/4077 |
| | | | | 204/427 |
| 2002/0008025 | A1 * | 1/2002 | Fujii | G01N 27/4077 |
| | | | | 204/429 |
| 2012/0036929 | A1 | 2/2012 | Fujita et al. | |
| 2012/0211362 | A1 * | 8/2012 | Onkawa | G01N 27/4077 |
| | | | | 204/424 |
| 2014/0291150 | A1 | 10/2014 | Otsuka et al. | |

FOREIGN PATENT DOCUMENTS

| | | |
|---|---|---|
| JP | 1-232252 A | 9/1989 |
| JP | 1-232253 A | 9/1989 |
| JP | 1-245147 A | 9/1989 |
| JP | 10-221296 A | 8/1998 |
| JP | 11072460 A | 3/1999 |
| JP | 2003-279528 A | 10/2003 |
| JP | 2012037445 A | 2/2012 |
| JP | 2012189579 A | 10/2012 |
| JP | 2013-104706 A | 5/2013 |

OTHER PUBLICATIONS

Office Action dated Oct. 25, 2017, by the Japanese Patent Office in counterpart Japanese Application No. 2014-157864.

* cited by examiner

GAS SENSOR ELEMENT AND GAS SENSOR

BACKGROUND OF THE INVENTION

1. Field of the Invention

The present invention relates to a gas sensor element and a gas sensor which detects a concentration of a detecting gas.

2. Description of the Related Art

A sensor in which a substantially cylindrical gas sensor element extending in an axial direction and having a closed front end is inserted into and held in a tubular main metal fitting has been known as a gas sensor which detects an oxygen concentration in an exhaust gas of a vehicle or the like (see JP 2012-37445A). This gas sensor element has a tubular solid electrolyte body (hereinafter, also referred to as an element main body), and an inside electrode and an outside electrode which are formed on inner and outer surfaces of the solid electrolyte body, respectively. The outer surface of the solid electrolyte body is covered with a porous protective layer for protecting the outside electrode from poisoning or the like (see JP-H11-72460A).

A technique has been developed in which in a gas sensor element provided with a porous protective layer on a lamination type (plate type) detection element, the porous protective layer includes three regions. Further, the inside region has a higher porosity than an outside region (see JP 2012-189579A).

In the porous protective layer of JP 2012-189579A, the porosity of the inside region is higher than the porosity of the outside region. Thus, a heat insulating effect of the inside region is increased, and loss of the heat of the detection element to the porous protective layer can be suppressed. On the other hand, since the porosity of the outside region is lower than the porosity of the inside region, a poisonous substance adhering to the porous protective layer can be effectively caught in the outside region. Further, water droplets adhering to the porous protective layer have difficulty penetrating the inside region, but can be allowed to effectively penetrate into the outside region. As a result, adhesion of the water droplets to the detection element can be suppressed.

In recent years, the porous protective layer of JP 2012-189579A has been considered for application to a tubular gas sensor element. However, this porous protective layer is easily peeled from a solid electrolyte body when applied to a tubular gas sensor element. The detection element of a lamination type (plate type) gas sensor element has a relatively lower strength than the solid electrolyte body of the tubular gas sensor element. Accordingly, when a gas sensor is formed by assembling the lamination type (plate type) gas sensor element to a main metal fitting and a vibration is imparted to the gas sensor, the detection element is bent together with the porous protective layer. Thus, the stress added only to the porous protective layer can be released.

On the other hand, the solid electrolyte body of the tubular gas sensor element has a relatively high strength. Accordingly, when a gas sensor is formed, the solid electrolyte body is not bent even when a vibration is imparted to the gas sensor. Therefore, the stress is added only to the porous protective layer, and thus the porous protective layer is easily peeled from the solid electrolyte body. Particularly, when a porous protective layer in which an inside region has a higher porosity than an outside region as in JP 2012-189579A is applied to the tubular gas sensor element, the porous protective layer is easily peeled at an interface with the solid electrolyte body.

SUMMARY OF THE INVENTION

Accordingly, an object of the present invention is to provide a gas sensor element and a gas sensor including a porous protective layer having an inside region and an outside region which is resistant to peeling even when covering a tubular gas sensor element.

The above object is achieved by providing, in a first aspect (1), a gas sensor element comprising: a solid electrolyte body having a bottomed tubular shape and a closed front end, and extending in an axial direction; an inside electrode which is provided on an inner surface of the solid electrolyte body; an outside electrode which is provided on an outer surface of the solid electrolyte body; and a porous protective layer which covers the outside electrode, wherein the porous protective layer includes an inside region which covers the outside electrode and an outside region which covers the inside region and has a lower porosity than the inside region, and the outside region is formed of a sintered body of ceramic and glass.

According to the gas sensor element (1), the outside region is formed of a sintered body of ceramic and glass. Accordingly, since the glass is melted upon firing of the outside region and is thus interposed between the ceramic particles, the bonding between the ceramic particles is strengthened. As a result, the strength of the outside region is improved and the strength of the porous protective layer is also improved. Further, even when stress is imparted to the porous protective layer, peeling of the porous protective layer from the solid electrolyte body can be suppressed.

Moreover, since the outside region is formed of a sintered body of ceramic and glass, the outside region has a relatively low porosity, but a relationship in which the porosity of the outside region is lower than the porosity of the inside region can be maintained. Accordingly, since the porosity of the outside region is maintained so as to be lower than the porosity of the inside region, a poisonous substance can be effectively captured in the outside region. Further, water droplets can effectively penetrate the outside region. On the other hand, since the porosity of the inside region is maintained so as to be higher than the porosity of the outside region, the inside region maintains a heat insulating effect. Further, loss of the heat of the solid electrolyte body to the porous protective layer can be suppressed.

The inside region may be formed of a sintered body of ceramic and glass, or a sintered body of ceramic only. Particularly, when the inside region is formed of a sintered body of ceramic and glass, the strength of the inside region is further improved. The adhesion between the inside region and the outside region is also further improved as compared to the case in which the inside region is formed of a sintered body of ceramic only.

In a preferred embodiment (2) of the gas sensor element (1) above, the outside region extends to a side closer to a rear end of the solid electrolyte body than the inside region and includes the inside region.

Since the outside region extends to a side closer to a rear end of the solid electrolyte body than the inside region and includes the inside region, the solid electrolyte body and the outside region are joined to each other. As a result, adhesion of the inside region to the outside region is improved, and adhesion to the solid electrolyte body with respect to the outside region is also improved. Peeling at an interface between the outside region and the inside region and at an interface between the outside region and the solid electrolyte body is also prevented.

In another preferred embodiment (3) of the gas sensor element (1) or (2) above, the ceramic of the outside region is formed of coarse particles having a large particle diameter and fine particles smaller than the coarse particles, and the outside region preferably contains the glass in an amount of 7.5 wt % to 12 wt %.

When the outside region is formed of coarse particles and fine particles, a structure can be made in which a larger amount of a poisonous substance is captured or a larger amount of water droplets penetrates the outside region. When the outside region formed of coarse particles and fine particles contains the glass in an amount of 7.5 wt % to 12 wt %, the bonding between the ceramic particles including the coarse particles and the fine particles is strengthened. As a result, the strength of the outside region is improved, and the strength of the porous protective layer is also improved.

When the content of the glass is less than 7.5 wt % in the outside region, an improvement in the strength of the outside region formed of the coarse particles and the fine particles may not be obtained. When the content of the glass is greater than 12 wt % in the outside region, residual stress remains in the glass due to the particle growth of the fine particles. Thus, an improvement in the strength of the outside region formed of the coarse particles and the fine particles may not be obtained.

In yet another preferred embodiment (4) of the gas sensor element (3) above, the inside region is formed of a sintered body of ceramic formed of the coarse particles and glass, and the glass is contained in the inside region in an amount of 9 wt % to 18 wt %.

When the inside region is formed using coarse particles which are used in the outside region, the porosity of the inside region can be made higher than that of the outside region. Thus, the inside region can effectively maintain a heat insulating effect. When the inside region formed of coarse particles contains the glass in an amount of 9 wt % to 18 wt %, the bonding between the coarse particles is strengthened. Thus, the strength of the inside region is improved, and the strength of the porous protective layer is also improved.

When the content of the glass is less than 9 wt % in the inside region, an improvement in the strength of the inside region formed of the coarse particles may not be obtained. When the content of the glass is greater than 18 wt % in the inside region, a large amount of glass is contained between the coarse particles. Thus, the porosity of the inside region becomes lower than that of the outside region, and the inside region may not maintain a heat insulating effect.

In yet another preferred embodiment (5) of the gas sensor element of any of (1) to (4) above, a sprayed layer which is formed by spraying is provided between the outside electrode and the porous protective layer, and the sprayed layer has a lower porosity than the porous protective layer.

Since a sprayed layer having a lower porosity than the porous protective layer is formed between the outside electrode and the porous protective layer, the adhesion between the porous protective layer and the element main body can be further improved. Moreover, since the sprayed layer has a lower porosity than the porous protective layer, diffusion of an exhaust gas can be controlled by the sprayed layer alone, and the functions (of capturing a poisonous substance, effective penetration of water droplets, and control of loss of the heat of the detection element to the porous protective layer) of the porous protective layer (the outside region and the inside region) can be sufficiently exhibited.

In a second aspect (6), the present invention provides a gas sensor comprising: a detection element as described in any of (1) to (5) above which detects a specific gas in a measuring gas; and a main metal fitting which holds the detection element.

Effects of the Invention

According to the invention, a gas sensor element can be obtained including a porous protective layer having an inside region and an outside region which is resistant to peeling even when covering a tubular gas sensor element.

DESCRIPTION OF REFERENCE NUMERALS

Reference numerals used to identify various features in the drawings include the following.
3: GAS SENSOR ELEMENT
3S: SOLID ELECTROLYTE BODY
20: MAIN METAL FITTING
50: INSIDE ELECTRODE
51: OUTSIDE ELECTRODE
60: SPRAYED LAYER
80: POROUS PROTECTIVE LAYER
81: INSIDE REGION
82: OUTSIDE REGION
100: GAS SENSOR
O: AXIAL DIRECTION

DETAILED DESCRIPTION OF THE PREFERRED EMBODIMENTS

Hereinafter, the invention will be described in detail with reference to the drawings. However, the present invention should not be construed as being limited thereto.

Figure 1:
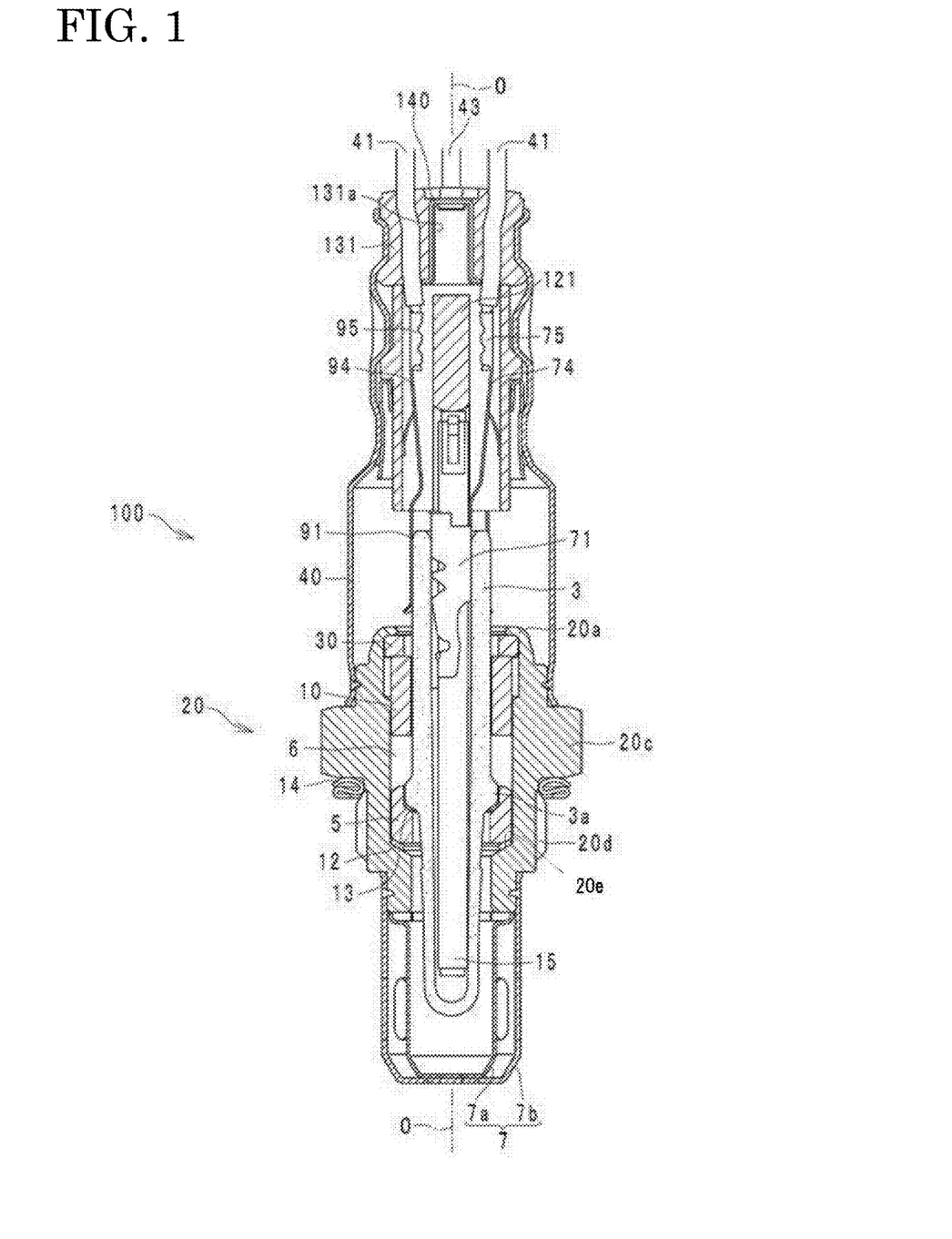
FIG. 1 is a cross-sectional view of a gas sensor according to an embodiment of the invention, cut by a plane in an axial direction.

FIG. 1 shows a cross-sectional view of a gas sensor 100 having a gas sensor element 3 according to an embodiment of the invention, cut by a plane in the direction of an axial line O. In this embodiment, the gas sensor 100 is an oxygen sensor which is inserted into an exhaust of a vehicle so that a front end thereof is exposed to an exhaust gas, thereby detecting an oxygen concentration of the exhaust gas. The gas sensor element 3 is a known oxygen sensor element which constitutes an oxygen concentration cell having a pair of electrodes laminated on an oxygen ion conductive solid electrolyte body, and which outputs a detection value according to an oxygen content.

The lower side of FIG. 1 corresponds to a front end side of the gas sensor 100, and the upper side of FIG. 1 corresponds to a rear end side of the gas sensor 100.

In the gas sensor 100, the substantially cylindrical (hollow shaft-shaped) gas sensor element (in this example, oxygen sensor element) 3 having a closed front end is assembled so as to be inserted into and held in a tubular metal fitting main body (main metal fitting) 20. The sensor element 3 is formed of a tubular solid electrolyte body 3s (see FIG. 2) which is reduced in diameter in a tapered shape toward the front end, and an inside electrode 50 (see FIG. 2) and an outside electrode 51 (see FIG. 2) which are formed on an inner circumferential surface and an outer circumferential surface of the solid electrolyte body 3s, respectively. A round bar-shaped heater 15 is inserted into the hollow portion of the gas sensor element 3 so that the temperature of the solid electrolyte body 3s is increased to an activation temperature.

A tubular outer casing 40 which holds lead wires and terminals both provided on the rear end side of the gas sensor element 3 (described below), and covers a rear end portion of the sensor element 3 is joined to a rear end portion of the metal fitting main body 20. A columnar insulating separator 121 is crimped and fixed to the inside of the outer casing 40 on the rear end side of the gas sensor element 3. A protector 7 covers a detection portion at the front end of the gas sensor element 3. By fitting a male screw portion 20d of the metal fitting main body 20 of the gas sensor 100 manufactured as described above into a screw hole of an exhaust or the like, the detection portion at the front end of the gas sensor element 3 is exposed to the inside of the exhaust, and detects a detecting gas (exhaust gas). A polygonal flange portion 20c for engaging a hexagonal wrench or the like is provided around the center of the metal fitting main body 20, and a gasket 14 which prevents gas leakage when the gas sensor is mounted in an exhaust pipe is fit into a step portion between the flange portion 20c and the male screw portion 20d.

An inner circumferential surface near the front end of the metal fitting main body 20 has a step portion 20e of reduced inward diameter. A tubular ceramic holder 5 is disposed on a rearward surface of the step portion 20e via a washer 12. The gas sensor element 3 is inserted into the metal fitting main body 20 and the ceramic holder 5, and a flange portion 3a provided on the central side of the gas sensor element 3 is brought into contact with the ceramic holder 5 via a washer 13 from the rear end side.

Furthermore, a tubular talc powder 6 and a tubular ceramic sleeve 10 are disposed in a gap in a radial direction between the gas sensor element 3 and the metal fitting main body 20 on the rear end side of the flange portion 3a. A metal ring 30 is disposed on the rear end side of the ceramic sleeve 10, and the rear end portion of the metal fitting main body 20 is bent inward to form a crimping portion 20a, and thus the ceramic sleeve 10 is pressed toward the front end. Accordingly, the talc powder 6 is compressed, the ceramic sleeve 10 and the talc powder 6 are crimped and fixed to each other, and the gap between the gas sensor element 3 and the metal fitting main body 20 is sealed.

The separator 121 disposed on the rear end side of the gas sensor element 3 is provided with insertion holes (in this example, four insertion holes), and plate-shaped base portions 74 and 94 of an inside terminal metal fitting 71 and an outside terminal metal fitting 91 are inserted into and fixed to two of the insertion holes. The plate-shaped base portions 74 and 94 have connector portions 75 and 95 formed at rear ends thereof, respectively, and lead wires 41 are crimped and connected to the connector portions 75 and 95. Heater lead wires 43 (in FIG. 1, only one is shown) drawn from the heater 15 are inserted into two insertion holes (heater lead holes) (not shown) of the separator 121.

A tubular grommet 131 is crimped and fixed to the inside of the outer casing 40 on the side closer to the rear end than the separator 121, and the two lead wires 41 and the two heater lead wires 43 are drawn to the outside from four insertion holes of the grommet 131.

The grommet 131 has an insertion hole 131a formed at the center thereof, and the insertion hole 131a communicates with the internal space of the gas sensor element 3. A water-repellent ventilation filter 140 is internally mounted in a through hole 131a of the grommet 131 to introduce a reference gas (atmosphere) to the internal space of the gas sensor element 3 without external water passing therethrough.

The tubular protector 7 is externally fitted on the front end side of the metal fitting main body 20, and thus the front end side of the gas sensor element 2 protruding from the metal fitting main body 20 is covered with the protector 7. The protector 7 is configured by attaching to each other by welding or the like double inside and outside protectors 7a and 7b made of a metal (for example, stainless steel) and having a bottomed tubular shape with a plurality of hole portions (not shown).

Figure 2:
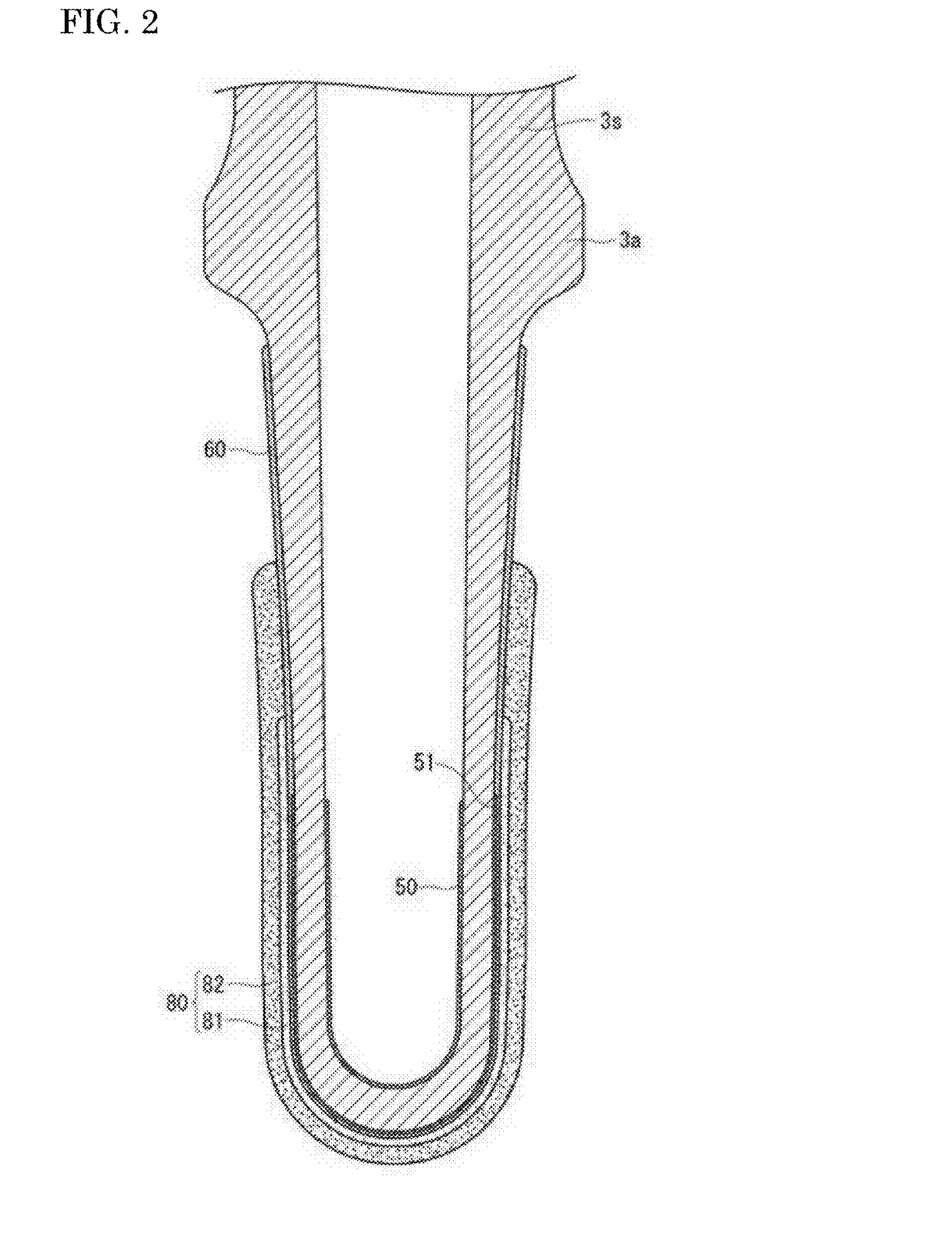
FIG. 2 is a partial cross-sectional view showing a configuration of a gas sensor element.

A configuration of the gas sensor element 3 will next be described with reference to FIG. 2. As shown in FIG. 2, at the front end side of the inner circumferential surface of the solid electrolyte body 3s, the inside electrode 50 is formed over the entire circumference including a front end surface in a circumferential direction. A lead portion (not shown) extends toward the rear end from the inside electrode 50. On the front end side of the outer circumferential surface of the solid electrolyte body 3s, the outside electrode 51 is formed over the entire circumference including a front end surface in the circumferential direction. A lead portion (not shown) extends toward the rear end from the outside electrode 51.

The inside electrode 50 is exposed to a reference gas atmosphere introduced to the internal space of the gas sensor element 3. The outside electrode 51 formed on the outer surface of the gas sensor element 3 is exposed to a detecting gas to perform gas detection between the inside electrode 50 and the outside electrode 51 via the solid electrolyte body 3s.

The inside electrode 50 and the outside electrode 51 are electrically connected to the inside terminal metal fitting 71 and the outside terminal metal fitting 91 via the lead portions (not shown), respectively.

A sprayed layer 60 is formed to cover the outside electrode 51 in a region from the front end surface of the outer circumferential surface of the solid electrolyte body 3s to the vicinity of the flange portion 3a. The sprayed layer 60 is formed by spraying a ceramic such as spinel, and is a porous layer.

A porous protective layer 80 covers the outside electrode 51 via the sprayed layer 60. The porous protective layer 80 has an inside region (inside layer) 81 and an outside region (outside layer) 82 arranged from the surface of the outside electrode 51 toward the outside. The inside region 81 extends to the side closer to the rear end than the outside electrode 51 and includes the outside electrode 51, and the outside region 82 extends to the side closer to the rear end than the inside region 81 and includes the inside region 81.

The inside region 81 can be formed by bonding one or more kinds of ceramic particles selected from the group consisting of alumina, spinel, zirconia, mullite, zircon and cordierite by firing or the like. By sintering a slurry containing these particles, pores can be formed between the ceramic particles.

The porosity of the inside region 81 is preferably 50% to 70%. In this embodiment, the porosity is 55%. The porosity of the inside region 81 is preferably 50% to 70% to give the inside region 81 a good heat insulating property. When the porosity of the inside region 81 is lower than 50%, a total pore volume is reduced, and thus its effect as a heat-insulating layer is reduced. When the porosity is higher than 70%, it may be difficult to constitute the inside region 81.

The thickness of the inside region 81 is preferably 100 µm to 800 µm.

The inside region 81 and the outside region 82 are determined as follows. First, based on a photograph (SEM image, see FIG. 3) of a cross-section of the porous protective layer 80, the inside region 81 and the outside region 82 are distinguished from each other in places where the ceramic particles have different sizes, particle shapes, pore shapes, and the like.

The porosity of each of the inside region 81 and the outside region 82 is obtained as follows. Using commercially available image analysis software, binarization is performed in a thickness direction of the outside region 82 and the inside region 81 based on a photograph (SEM image, FIG. 3) of a cross-section of the porous protective layer 80 to obtain a ratio of black portions in the photograph of the cross-section. In the photograph of the cross-section, the black portions correspond to pores and white portions correspond to the ceramic and the glass (sintered body thereof). Accordingly, the more the black portions, the higher the porosity.

Figure 3:
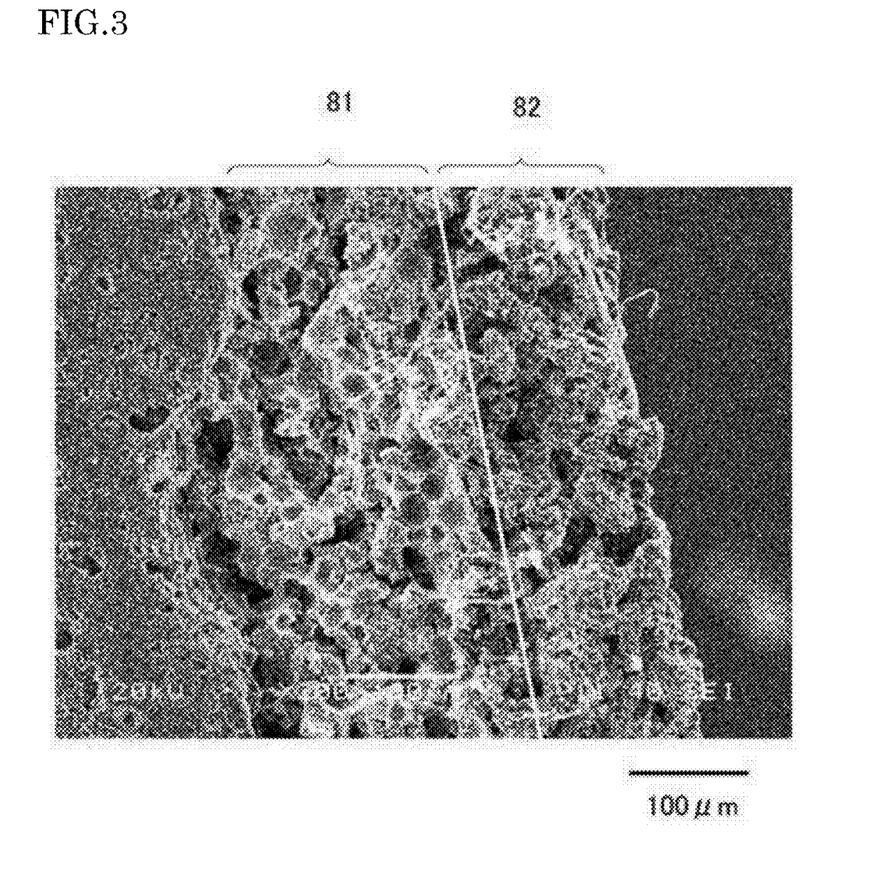
FIG. 3 is a view showing a cross-section SEM image of a porous protective layer of an example.

When the porosity is obtained in the thickness direction (horizontal direction in FIG. 3) of the outside region 82 and the inside region 81 of FIG. 3, a part corresponding to the inside region 81 exhibits a predetermined porosity within a fixed variation range, but in a certain place, the variation is exceeded and the porosity is reduced. Therefore, this place can be regarded as a boundary between the inside region 81 and the outside region 82 (the white line in FIG. 3), and the layer on the outside of this place is the outside region 82.

The outside region 82 can be formed by firing, for example, one or more kinds of ceramic particles selected from the group consisting of alumina, spinel, zirconia, mullite, zircon, and cordierite and glass.

By sintering a slurry containing the ceramic particles, gaps are formed between the ceramic particles, or when an organic or inorganic binder in the slurry burns off, pores are formed between the ceramic particles. In addition, since the glass is melted upon firing of the outside region 82 and is thus interposed between the ceramic particles, the bonding between the ceramic particles is strengthened. As a result, the strength of the outside region 82 is improved and the strength of the porous protective layer 80 is also improved. Accordingly, even when stress is imparted to the porous protective layer 80, peeling from the solid electrolyte body 3s can be suppressed. Moreover, since adhesion of the inside region 81 to the outside region 82 is improved, and the outside region 82 extends to the side closer to the rear end than the inside region 81 and includes the inside region 81, adhesion to the solid electrolyte body 3s with respect to the outside region 82 is improved. Further, peeling at an interface between the outside region 82 and the inside region 81 and at an interface between the outside region 82 and the solid electrolyte body 3s is prevented.

The porosity of the outside region 82 is preferably 25% to 40%. In this embodiment, the porosity is 30%. The porosity of the outside region 82 is preferably 25% to 40% so as to allow for the capture of a poisonous substance and penetration of water droplets, and gas permeability is not reduced. When the porosity of the outside region 82 is lower than 25%, clogging easily occurs due to a poisonous substance. When the porosity is higher than 40%, water may penetrate into the outside region 82 and water repellency may be reduced.

The thickness of the outside region 82 is preferably 100 μm to 800 μm.

When the porosity of the outside region 82 is lower than the porosity of the inside region 81, a poisonous substance can be effectively captured in the outside region 82, and water droplets adhering to the porous protective layer 80 hardly penetrate the inside region 81 and can be allowed to effectively penetrate into the outside region 82. In addition, when the porosity of the inside region 81 is higher than the porosity of the outside region 82, a heat insulating effect of the inside region 81 is increased, and loss of the heat of the solid electrolyte body 3s to the porous protective layer 80 can be suppressed.

The pores formed in the porous protective layer 80 constitute a three-dimensional network structure so that gas transmission is possible.

In addition, the thickness of the inside region 81 is preferably larger than the thickness of the outside region 82. Accordingly, the amount of water droplets penetrating the outside region 82 can be increased, and the amount of a captured poisonous substance can also be increased.

Furthermore, in this embodiment, the ceramic particles of the outside region 82 are formed of coarse spinel particles having a large particle diameter and fine titania particles smaller than the coarse particles. When the outside region 82 is formed of coarse particles and fine particles, a structure can be made in which a larger amount of a poisonous substance is captured or a larger amount of water droplets penetrates the outside region 82. The outside region 82 formed of coarse particles and fine particles preferably contains 7.5 wt % to 12 wt % of glass. In this embodiment, 8 wt % of glass is contained. When the outside region 82 contains 7.5 wt % to 12 wt % of glass, the bonding between the ceramic particles including the coarse particles and the fine particles is strengthened. As a result, the strength of the outside region 82 is improved and the strength of the porous protective layer 80 is also improved.

In this embodiment, the ceramic particles of the inside region 81 are formed using coarse spinel particles which are used in the outside region 82. When the inside region 81 is formed using coarse particles which are used in the outside region 82, the porosity of the inside region 81 can be made higher than that of the outside region 82. Thus, the inside region 81 can effectively maintain a heat insulating effect.

The inside region formed using coarse particles preferably contains 9 wt % to 18 wt % of glass. In this embodiment, 10 wt % of glass is contained. When the inside region 81 contains 9 wt % to 18 wt % of glass, the bonding between the particles is strengthened, and thus the strength of the inside region is improved and the strength of the porous protective layer is also improved.

In this embodiment, the porosity of the sprayed layer 60 is lower than the porosity of the porous protective layer 80. The porosity of the sprayed layer 60 is preferably 5% to 20%. In this embodiment, the porosity is 15%.

Since the sprayed layer 60 having a lower porosity than the porous protective layer 80 is formed between the outside electrode 51 and the porous protective layer 80, adhesion between the porous protective layer 80 and the solid electrolyte body 3s can be further improved. Moreover, since the sprayed layer 60 has a lower porosity than the porous protective layer 80, diffusion of exhaust gas can be controlled by the sprayed layer 60 alone, and the functions (of capturing a poisonous substance, effective penetration of water droplets, and control of loss of the heat of the detection element to the porous protective layer) of the porous protective layer 80 (the outside region 82 and the inside region 81) can be sufficiently exhibited.

An average pore diameter (A) of the sprayed layer 60, an average pore diameter (B) of the outside region 82, and an average pore diameter (C) of the inside region 81 preferably satisfies a relationship of A<B<C. Accordingly, the functions of each of the sprayed layer 60 and the porous protective layer 80 (the outside region 82 and the inside region 81) can be sufficiently exhibited.

Next, an example of a method of manufacturing the gas sensor element according to the embodiment of the invention will be described.

First, a slurry of materials of a predetermined solid electrolyte (for example, partially stabilized zirconia in which 5 mol % of $Y_2O_3$ is added to $ZrO_2$) is prepared, and this slurry is dried and granulated using a spray dry method. The resulting powder is formed into a bottomed cylindrical shape using a hydraulic pressing method, and ground into a predetermined shape. Then, the resulting object is fired, for example, at 1500° C. to form the solid electrolyte body 3s.

Next, using an electroless plating method, the inside electrode 50 made of Pt is formed on the inner circumferential surface of the solid electrolyte body 3s. Similarly, using the electroless plating method, the outside electrode 51 made of Pt is formed on the front end side of the outer circumferential surface of the solid electrolyte body 3s.

Next, the ceramic (spinel or the like) sprayed layer 60 is formed to cover the outside electrode 51.

Next, a ceramic-containing inside paste to become the inside region 81 is applied onto the sprayed layer 60 to cover the outside electrode 51, and is fired. The inside paste can be applied by a dipping method.

Next, an outside paste that becomes the outside region 82 is applied to the surface of the inside paste, and is fired. A slurry for forming the outside paste contains ceramic and glass. Respective slurries for forming the inside region 81 and the outside region 82 may be applied in order and then sintered at one time.

The invention is not limited to the above-described embodiments, and may cover various modifications and equivalents included within the spirit and scope of the claims appended hereto. For example, the shape of the inside electrode is not limited to that described above.

EXAMPLES

Example 1

A solid electrolyte body 3s formed of partially stabilized zirconia, in which 5 mol % of $Y_2O_3$ was added to $ZrO_2$, and having a bottomed cylindrical shape as shown in FIGS. 1 and 2 was prepared. Next, an inside electrode 50 made of Pt was formed on an inner circumferential surface of the solid electrolyte body 3s using an electroless plating method. Similarly, an outside electrode 51 made of Pt was formed on the front end side of an outer circumferential surface of the solid electrolyte body 3s using the electroless plating method.

Next, a ceramic (spinel or the like) sprayed layer 60 was formed (thickness: 150 μm) to cover the outside electrode 51.

Next, using a dipping method, an inside paste that becomes an inside region 81 was applied (thickness: 250 μm) onto the sprayed layer 60 to cover the outside electrode 51. In the inside paste, only spinel (average particle diameter: 30 μm) was used as ceramic particles, and in this embodiment, glass was not added to the inside paste.

Next, an outside paste that becomes an outside region 82 was applied (thickness: 450 μm) to a surface of the inside paste, and the entire outside paste was fired at 1000° C. To prepare a slurry for forming the outside paste, spinel (average particle diameter: 30 μm) and titania (average particle diameter: 0.1 μm) were mixed at a mixing ratio of 70 vol % of spinel and 30 vol % of titania to prepare ceramic particles, and glass formed of zircon-based glass was further mixed therein at a mixing ratio (mass ratio) of 8 wt % of glass to 100 wt % of ceramic. The glass transition temperature (approximately 600° C.) of the glass was lower than 1000° C. In this manner, a gas sensor element was manufactured in which a porous protective layer 80 (the inside region 81 and the outside region 82) was formed on a surface of the solid electrolyte body 3s.

For comparison, an inside region 81 and an outside region 82 were similarly formed using an outside paste containing no glass, and a gas sensor element was manufactured.

The gas sensor element thus obtained was attached to a pendulum impact test apparatus. In this test apparatus, the gas sensor element as a sample is lifted in a pendulum manner, and then subjected to free fall to allow the porous protective layer 80 of the gas sensor element to collide with, from a side surface, a protrusion of an opposite material (carbon tool steel SK120) attached perpendicularly just below a fulcrum. After the collision, the presence or absence of cracks in the porous protective layer 80 was visually observed for evaluation using the following criteria. The higher the lifting angle of the pendulum, the greater the impact.

O: The porous protective layer had no cracks.
X: Cracks were generated in the porous protective layer.

The results thus obtained are shown in Table 1.

TABLE 1

| | Lifting Angle of Pendulum | | | | |
|---|---|---|---|---|---|
| | 20° | 30° | 40° | 50° | 60° |
| Comparative Example | O | X | Not conducted | Not conducted | Not conducted |
| Example | O | O | O | O | X |

As seen from Table 1, in the case of the example in which the outside region was formed of a sintered body of ceramic and glass, the porous protective layer had no cracks even when the lifting angle of the pendulum was high (50 degrees). In contrast, in the comparative example, cracks were generated in the porous protective layer when the lifting angle of the pendulum was 30 degrees.

Example 2

A solid electrolyte body 3s similar to that of Example 1 was prepared, and similarly to Example 1, an inside electrode 50, an outside electrode 51 and a sprayed layer 60 were formed.

Next, by a dipping method, an inside paste to be an inside region 81 was applied (thickness: 250 μm) onto the sprayed layer 60 to cover the outside electrode 51. In the inside paste, only spinel (average particle diameter: 30 μm) was used as the ceramic particles, and in this embodiment, glass formed of zircon-based glass was further mixed therein at a mixing ratio (mass ratio) of 10 wt % of glass to 100 wt % of ceramic.

Next, an outside paste to be an outside region 82 was applied (thickness: 450 μm) to a surface of the inside paste, and the entire outside paste was fired at 1000° C. To prepare a slurry for forming the outside paste, spinel (average particle diameter: 30 μm) and titania (average particle diameter: 0.1 μm) were mixed at a mixing ratio of 70 vol % of spinel and 30 vol % of titania to prepare ceramic particles, and glass formed of zircon-based glass was further mixed therein at a mixing ratio (mass ratio) shown in Table 2 to 100 wt % of ceramic. In this manner, a gas sensor element was manufactured in which a porous protective layer 80 (the inside region 81 and the outside region 82) was formed on a surface of the solid electrolyte body 3s.

An adhesion evaluation was performed on the obtained gas sensor element. As the adhesion evaluation, the gas sensor element was disposed in the ambient atmosphere, and a cycle of: heating the sensor element for 90 seconds (temperature that the element reached: 950° C.); leaving the sensor element to cool for 90 seconds; and subjecting the sensor element to air cooling for 90 seconds, was repeated 50 times. The surface of the porous protective layer 80 of the gas sensor element after 50 cycles was observed with a magnifying glass, and the presence or absence of cracks in the porous protective layer 80 was evaluated with the same criteria as in Example 1.

The obtained results are shown in Table 2.

TABLE 2

| | Glass Content | | | | | | | | |
|---|---|---|---|---|---|---|---|---|---|
| | 5 wt % | 7 wt % | 7.3 wt % | 7.5 wt % | 8 wt % | 9 wt % | 10 wt % | 12 wt % | 15 wt % |
| Adhesion | X | X | X | ○ | ○ | ○ | ○ | ○ | X |

○: no cracks present
X: cracks present

As is clear from Table 2, when the glass content of the outside region was 7.3 wt % or lower or 15 wt % or higher, cracks were generated in the porous protective layer. When the glass content of the outside region was 7.5 wt % to 12 wt %, no cracks were generated in the porous protective layer.

Example 3

A solid electrolyte body 3s similar to that of Example 2 was prepared, and similarly to Example 2, an inside electrode 50, an outside electrode 51 and a sprayed layer 60 were formed.

Next, by a dipping method, an inside paste that becomes an inside region 81 was applied (thickness: 250 μm) onto the sprayed layer 60 to cover the outside electrode 51, and the entire inside paste was fired at 1000° C. In the inside paste, only spinel (average particle diameter: 30 μm) was used as the ceramic particles, and in this embodiment, glass formed of zircon-based glass was further mixed therein at a mixing ratio (mass ratio) shown in Table 3 to 100 wt % of ceramic. In this manner, a gas sensor element was manufactured in which the inside region 81 was formed on a surface of the solid electrolyte body 3s.

The adhesion evaluation was performed on the gas sensor element thus obtained. A similar evaluation to that of Example 2 was performed as the adhesion evaluation. The results thus obtained are shown in Table 3.

In addition, a responsiveness evaluation was performed on the above-described gas sensor element. Specifically, a gas sensor was prepared by assembling the gas sensor element to a main metal fitting or the like. This gas sensor was attached to an exhaust of an in-line four cylinder gasoline engine having a displacement of 2000 CC to measure an output value thereof. The gasoline engine was driven at a speed of 200 rpm (number of rotations/min) using unleaded gasoline. The exhaust temperature was approximately 450° C. In this measurement, when a theoretical air fuel ratio of 14.7:1 was set to $\lambda=1$, control was forcibly performed for switching between rich ($\lambda=0.97$) and lean ($\lambda=1.03$) at 0.5 Hz. In addition, the sum of a time until the output of the gas sensor was changed to a value corresponding to $\lambda=1$ after switching from rich to lean, and a time until the output of the gas sensor was changed to a value corresponding to $\lambda=1$ after switching from lean to rich was obtained. The evaluation was performed using the following criteria.

○: A delay of less than 40 ms occurred compared to a conventional product (a gas sensor with an inside region 81 containing no glass).

X: A delay of 40 ms or greater occurred compared to a conventional product (a gas sensor with an inside region 81 containing no glass).

The results thus obtained are shown in Table 3.

TABLE 3

| | Glass Content | | | | | | | | |
|---|---|---|---|---|---|---|---|---|---|
| | 1 wt % | 5 wt % | 7 wt % | 9 wt % | 10 wt % | 15 wt % | 18 wt % | 20 wt % | 50 wt % |
| Adhesion | X | X | X | ○ | ○ | ○ | ○ | ○ | ○ |
| Responsiveness | ○ | ○ | ○ | ○ | ○ | ○ | ○ | X | X |

As seen from Table 3, when the glass content of the outside region was 7 wt % or less, cracks were generated in the porous protective layer, but when the glass content of the outside region was 9 wt % or greater, no cracks were generated in the porous protective layer. In addition, when the glass content of the inside region was 20 wt % or greater, a delay of 40 ms or greater occurred as compared to a conventional product, but when the glass content of the inside region was 18 wt % or less, a delay of 40 ms or greater did not occur as compared to a conventional product.

This application is based upon and claims the benefit of Japanese Patent Application No. 2013-183868 filed on Sep. 5, 2013 and Japanese Patent Application No. 2014-157864 filed on Aug. 1, 2014, the contents of which are incorporated herein by reference in its entirety.

What is claimed is:

1. A gas sensor element comprising:
   a solid electrolyte body having a bottomed tubular shape and a closed front end, and extending in an axial direction;
   an inside electrode which is provided on an inner surface of the solid electrolyte body; an outside electrode which is provided on an outer surface of the solid electrolyte body; and
   a porous protective layer which covers the outside electrode,
   wherein the porous protective layer includes, in the following order from the outside electrode, a sprayed layer formed by spraying which covers the outside electrode, an inside layer which covers the sprayed layer, and an outside layer which covers the inside layer,
   the sprayed layer is formed of ceramic,
   the inside layer is formed of a sintered body of ceramic formed of coarse particles and glass,
   the outside layer is formed of a sintered body of ceramic and glass, the sprayed layer has a lower porosity than the outside layer,
the outside layer has a lower porosity than the inside layer,
the sprayed layer directly contacts the outside electrode,
the inside layer directly contacts the layer,
the outside layer directly contacts the inside layer,
the ceramic of the outside layer is formed of coarse particles having a large particle diameter and fine particles smaller than the coarse particles,
the outside layer contains the glass in an amount of 7.5 wt % to 12 wt % based on 100 wt % of the ceramic of the outside layer, and
the inside layer contains the glass in an amount of 9 wt % to 18 wt % based on 100 wt % of the ceramic of the inside layer.

2. The gas sensor element as claimed in claim 1,
wherein the outside layer extends to a side closer to a rear end of the solid electrolyte body than the inside layer and includes the inside layer.

3. A gas sensor comprising:
the detection element as claimed in claim 1 which detects a specific gas in a measuring gas; and
a main metal fitting which holds the detection element.

4. The gas sensor element as claimed in claim 1,
wherein the porosity of the inside layer is 50% to 70%.

5. The gas sensor element as claimed in claim 1,
wherein the porosity of the outside layer is 25% to 40%.

6. The gas sensor element as claimed in claim 4,
wherein the porosity of the outside layer is 25% to 40%.

7. The gas sensor element as claimed in claim 1,
wherein the porosity of the sprayed layer is 5% to 20%.

8. The gas sensor element as claimed in claim 7,
wherein the porosity of the inside layer is 50% to 70%.

9. The gas sensor element as claimed in claim 7,
wherein the porosity of the outside layer is 25% to 40%.

10. The gas sensor element as claimed in claim 8,
wherein the porosity of the outside layer is 25% to 40%.

* * * * *